United States Patent
Okamura

(10) Patent No.: US 7,460,643 B2
(45) Date of Patent: Dec. 2, 2008

(54) RADIOGRAPHIC APPARATUS AND RADIATION DETECTION SIGNAL PROCESSING METHOD

(75) Inventor: Shoichi Okamura, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/654,506

(22) Filed: Jan. 18, 2007

(65) Prior Publication Data

US 2007/0189446 A1   Aug. 16, 2007

(30) Foreign Application Priority Data

Feb. 14, 2006   (JP) .............................. 2006-036613

(51) Int. Cl.
 *H05G 1/00*  (2006.01)
(52) U.S. Cl. ........................................ 378/98.8; 378/19
(58) Field of Classification Search ................ 378/98.8, 378/4, 19, 207, 95, 210
See application file for complete search history.

(56) References Cited

U.S. PATENT DOCUMENTS 5,249,123 A   9/1993   Hsieh

2005/0031088 A1*   2/2005   Okamura et al. ............ 378/210

FOREIGN PATENT DOCUMENTS

| CN | 1579330 A | 2/2005 |
|---|---|---|
| JP | 2004-242741 | 9/2004 |

OTHER PUBLICATIONS

Chinese Office Action for the Application No. 200710005251.9 dated Jun. 13, 2008.

* cited by examiner

*Primary Examiner*—Hoon Song
(74) *Attorney, Agent, or Firm*—Cheng Law Group PLLC

(57) ABSTRACT

Corrected X-ray detection signals are obtained by removing lag-behind parts through a recursive computation based on initial values determined from lag signal value (step T2). Thus, the lag-behind parts can be removed by taking into consideration lag signal values remaining at a starting point of the recursive computation. The lag signal values are dependent on the characteristic of an FPD (flat panel X-ray detector). By removing the lag-behind parts, with the lag signal values taken into consideration, the lag-behind parts are removed from X-ray detection signals with increased accuracy, without being influenced by the characteristic of the FPD.

19 Claims, 5 Drawing Sheets

RADIOGRAPHIC APPARATUS AND RADIATION DETECTION SIGNAL PROCESSING METHOD

BACKGROUND OF THE INVENTION

(1) Field of the Invention

This invention relates to a radiographic apparatus for medical or industrial use and a radiation detection signal processing method, for obtaining radiographic images based on radiation detection signals outputted at predetermined sampling time intervals from a radiation detecting device as radiation is emitted to an object under examination. More particularly, the invention relates to a technique for eliminating time lags, due to the radiation detecting device, of the radiation detection signals taken from the radiation detecting device.

(2) Description of the Related Art

In a medical X-ray diagnostic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, the X-ray diagnostic apparatus is constructed to obtain an X-ray image corresponding to an X-ray penetration image of a patient for every period between sampling intervals, based on X-ray detection signals for one X-ray image taken at sampling time intervals from the FPD as the patient is irradiated with X rays from the X-ray tube. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive lag-free radiation detection signal $x_k$ with a lag-behind part removed from radiation detection signal $y_k$:

$$x_k = [y_k - \Sigma_{n=1}^{N}\{\alpha_n \cdot [1-\exp(T_n)] \cdot \exp(T_n) \cdot S_{nk}\}]/\Sigma_{n=1}^{N}\beta_n$$

in which $T_n = -\Delta t/\tau_n$, $S_{nk} = x_{k\_1} + \exp(T_n) \cdot S_{n(k\_1)}$, and $\beta_n = \alpha_n \cdot [1-\exp(T_n)]$, where $\Delta t$: sampling intervals;

k: subscript representing a k-th point of time in a sampling time series;

N: the number of exponential functions with different time constants forming the impulse response;

n: subscript representing one of the exponential functions forming the impulse response;

$\alpha_n$: intensity of exponential function n; and $\tau_n$: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated.

Then, Inventors have proposed a technique disclosed in Japanese Unexamined Patent Publication No. 2004-242741. This technique, in dealing with the time lags of the FPD, removes a lag-behind part due to an impulse response based on the following recursive equations a-c:

$$X_k = Y_k - \Sigma_{n=1}^{N}\{\alpha_n \cdot [1-\exp(T_n)] \cdot \exp(T_n) \cdot S_{nk}\} \qquad a$$

$$T_n = -\Delta t/\tau_n \qquad b$$

$$S_{nk} = X_{k\_1} + \exp(T_n) \cdot S_{n(k\_1)} \qquad c$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

In the above recursive computation, coefficients of the impulse response of the FPD, N, $\alpha_n$ and $\tau_n$, are determined in advance. With the coefficients fixed, radiation detection signal $Y_k$ is applied to equations a-c, thereby obtaining a lag-free radiation detection signal $X_k$.

Initial values are set for the recursive computation as follows. A setting k=0 is made, and $X_0=0$ in equation a and $S_{n0}=0$ in equation c are set as initial values before X-ray emission. Where the number of exponential functions is three (N=3), $S_{10}$, $S_{20}$ and $S_{30}$ are all set to 0.

In determining initial values in this way, an assumption is made that no residual lag (i.e. lag signal value) due to a time lag exists in time of X-ray non-irradiation (k=0: first frame) which is the starting point of the recursive computation. This aspect will particularly be described hereinafter. FIG. 6 is a view showing a state of radiation incidence. FIG. 7 is a view showing a time delay corresponding to the radiation incidence of FIG. 6. FIG. 8 is a view showing a time lag situation where a lag (i.e. a lag-behind part) in radiography overlaps fluoroscopy. In the drawings, time t0-t1 represents incidence for radiography, and time t2-t3 incidence for fluoroscopy.

As shown in FIG. 6, when an incidence of X rays takes place during time t2-t3, lag-behind parts shown in hatching in FIG. 7 add to a normal signal corresponding to an incident dose. This results in a radiation detection signal $Y_k$ shown in thick lines in FIG. 7. The above technique disclosed in Japanese Unexamined Patent Publication No. 2004-242741 can remove the lag-behind parts, i.e. the hatched portions in FIG. 7, to obtain a proper signal.

In time of starting fluoroscopy, there is hardly any lag remaining from a preceding event as shown in FIG. 7. Thus, the above technique disclosed in Japanese Unexamined Patent Publication No. 2004-242741 has no problem in carrying out a correction for removing the lag-behind parts (called "lag correction") with no problem.

However, such a lag characteristic is variable with sensors of the FPDs. With a sensor having large lags, a long-lasting lag resulting from a preceding process of fluoroscopy may overlap a next signal as an afterimage. When fluoroscopy is resumed immediately after radiography, as shown in FIG. 8, a lag of the radiography done during time t0-t1 overlaps the fluoroscopy (see k=0 in FIG. 8). In such a case, the prior technique disclosed in Japanese Unexamined Patent Publication No. 2004-242741 cannot cope with the problem. Then, sensors with a bad lag characteristic must be rejected as unacceptable.

SUMMARY OF THE INVENTION

This invention has been made having regard to the state of the art noted above, and its object is to provide a radiographic apparatus and a radiation detection signal processing method for accurately eliminating time lags, due to a radiation detecting device, of radiation detection signals taken from the radiation detecting device, without being influenced by the characteristic of the radiation detection device.

The above object is fulfilled, according to this invention, by a radiographic apparatus for obtaining radiographic images based on radiation detection signals, comprising:

a radiation emitting device for emitting radiation toward an object under examination;

a radiation detecting device for detecting radiation transmitted through the object under examination; and a signal sampling device for taking radiation detection signals from the radiation detecting device at predetermined sampling time intervals;

the apparatus obtaining radiographic images based on the radiation detection signals outputted from the radiation detecting device at the predetermined sampling time intervals as radiation is emitted to the object under examination;

the apparatus further comprising:

a time lag removing device for removing lag-behind parts from the radiation detection signals by a recursive computation, on an assumption that a lag-behind part included in each of the radiation detection signals taken at the predetermined sampling time intervals is due to an impulse response formed of a single exponential function or a plurality of exponential functions with different attenuation time constants; and an initial value determining device for determining initial values for the recursive computation based on lag signal values remaining at a starting point of the recursive computation;

wherein the time lag removing device is arranged to obtain corrected radiation detection signals by removing the lag-behind parts from the radiation detection signals through the recursive computation based on the initial values determined by the initial value determining device.

With the radiographic apparatus according to this invention, radiation detection signals are outputted from the radiation detecting device at predetermined sampling time intervals as radiation is emitted from the radiation emitting device to an object under examination. The time lag removing device removes a lag-behind part included in each of the radiation detection signals as due to an impulse response formed of a single exponential function or a plurality of exponential functions with different attenuation time constants. A recursive computation is performed when removing the lag-behind parts from the radiation detection signals. The initial value determining device determines initial values for the recursive computation based on lag signal values remaining at a starting point of the recursive computation. The time lag removing device obtains corrected radiation detection signals by removing the lag-behind parts from the radiation detection signals through the recursive computation based on the initial values determined by the initial value determining device. A radiographic image is obtained from the corrected radiation detection signals.

Thus, with the radiographic apparatus according to this invention, the time lag removing device removes lag-behind parts through the recursive computation based on the initial values determined by the initial value determining device, thereby to obtain corrected radiation detection signals. The lag-behind parts can be removed by taking into consideration lag signal values remaining at the starting point of the recursive computation. The lag signal values are dependent on the characteristic of the radiation detecting device. By removing the lag-behind parts, with the lag signal values taken into consideration, the lag-behind parts are removed from the radiation detection signals with increased accuracy, without being influenced by the characteristic of the radiation detecting device. Even where the radiation detecting device has a somewhat poor lag characteristic, the invention provides also an advantage of reducing the lag-behind parts to a quantity negligible for practical purposes, to enlarge a permissible range of the lag characteristic of the radiation detecting device, and improve the yield of the radiation detecting device.

In the above radiographic apparatus, the time lag removing device, preferably, is arranged to perform the recursive computation for removing the lag-behind part from each of the radiation detection signals, based on the following equations A-C:

$$X_k = Y_k - \Sigma_{n=1}^{N}[S_{nk}] \quad\quad\quad A$$

$$T_n = -\Delta t/\tau_n \quad\quad\quad B$$

$$S_{nk} = \exp(T_n) \cdot \{\alpha_n \cdot [1-\exp(T_n)] \cdot \exp(T_n) \cdot S_{n(k\_1)}\} \quad\quad\quad C$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n; and the initial value determining device is arranged to derive the initial values from the following equation D:

$$X_0 = 0, S_{n0} = \gamma_n \cdot Y_0 \quad\quad\quad D$$

where $\gamma_n$: residual rate of component n of a certain attenuation time constant $\tau_n$; and $Y_0$: lag signal value remaining at an X-ray non-emission time which is the starting point of the recursive computation;

and obtain the corrected radiation detection signals by removing the lag-behind parts based on the impulse response derived from equations A-C, with conditions of the initial values determined from equation D.

Where the recursive computation for removing the lag-behind part from each of the radiation detection signals is performed based on equations A-C, the corrected, lag-free radiation detection signals can be derived promptly from equations A-C constituting a compact recurrence formula. When, as shown in FIG. 6, for example, a fixed quantity of radiation enters the radiation detecting device during time t2-t3, and provided that no time lag occurs with the radiation detecting device, the X-ray detection signal will have a fixed value as shown in FIG. 6.

In practice, however, the radiation detecting device has a time lag to add a lag-behind part as shown in hatching in FIG. 7. Consequently, the X-ray detection signal $Y_k$ becomes as shown in thick lines in FIG. 7. Where the recursive computation for removing the lag-behind part from each of the radiation detection signals is performed based on equations A-C, the second term at the right side in equation A, that is equation C "$S_{nk} = \exp(T_n) \cdot \{\alpha_n \cdot [1 - \exp(T_n)] \cdot \exp(T_n) \cdot S_{n(k-1)}\}$" corresponds to each lag-behind part shown in hatching in FIG. 7. Since the lag-behind part is deducted from radiation detection signal $Y_k$, the corrected radiation detection signal $X_k$ is free from the lag-behind part as shown in FIG. 6.

When, as shown in FIG. 8, a lag of photography performed during time t0-t1 overlaps fluoroscopy, a residual lag (lag signal value) due to a lag-behind part generated in the photography during time t0-t1 exists even at a radiation non-emission time (k=0 in FIG. 8) which is a starting point of the recursive computation. That is, even though this is a radiation non-emission time, the initial value $Y_0$ of radiation detection signal $Y_k$ is not 0. Thus, initial values for the recursive computation are set to $X_0 = 0$ and $S_{n0} = \gamma_n \cdot Y_0$ as in equation D ($Y_0$: lag signal value remaining at the radiation non-emission time which is a starting point of the recursive computation). With the conditions of the initial values derived from equation D, the lag-behind part is removed based on the impulse response derived from equations A-C, to obtain a corrected radiation detection signal.

By removing the lag-behind parts, with the lag signal values taken into consideration as in equation D, the lag-behind parts are removed from radiation detection signals with increased accuracy, without being influenced by the characteristic of the radiation detecting device.

A preferred example of setting each residual rate $\gamma_n$ is as follows. Each residual rate $\gamma_n$ is set to satisfy conditions of the following equation E:

$$\Sigma_{n=1}^{N}[\gamma_n] \leq 1, 0 \leq \gamma_n \quad \text{E}$$

where $\Sigma_{n=1}^{N}[\gamma_n]$: total of residual rates $\gamma_n$ of component n.

When the total of residual rates $\gamma_n$ of component n exceeds 1, the lag-behind parts can be removed excessively. Conversely, when the total of residual rates $\gamma_n$ of component n has a negative value, the lag-behind parts can be added. The lag-behind parts may be removed in an appropriate amount by setting the total of residual rate $\gamma_n$ of component n to 0 to 1 inclusive, and setting residual rate $\gamma_n$ to 0 or more.

A more specific, preferred example of setting each residual rate $\gamma_n$ is as follows. Equation E is set to satisfy conditions of $$\Sigma_{n=1}^{N}[\gamma_n] = 1 \quad \text{E'}$$

and each residual rate $\gamma_n$ is set to satisfy conditions of $$\gamma_1 = \gamma_2 = \ldots = \gamma_n = \ldots = \gamma_{N-1} = \gamma_N \quad \text{F}$$

whereby equation D is expressed by the following equation D':

$$S_{n0} = Y_0/N \quad \text{D'}$$

Equation F is substituted into equation E' to obtain $N \cdot \gamma_N = 1$. Therefore, each residual rate $\gamma_n$ becomes $\gamma_N = 1/N$, and residual rates $\gamma_n$ are evenly distributed by the number N of exponential functions (with different time constants constituting the impulse response). Thus, by substituting $\gamma_N = 1/N$ for $S_{n0} = \gamma_n \cdot Y_0$ in equation D, equation D' is established.

Another specific, preferred example of setting each residual rate $\gamma_n$ is as follows. Equation E is set to satisfy conditions of $$\Sigma_{n=1}^{N}[\gamma_n] < 1 \quad \text{E''}$$

and residual rate $\gamma_M$ in component m of certain attenuation time constant $\tau_m$ and other residual rates $\gamma_N$ are set to satisfy the following expression G:

$$0 < \gamma_M < 1, \gamma_N = 0 \quad \text{G}$$

In the radiographic apparatus, one example of the radiation detecting device is a flat panel X-ray detector having numerous X-ray detecting elements arranged longitudinally and transversely on an X-ray detecting surface.

The radiographic apparatus according to this invention may be a medical apparatus, and an apparatus for industrial use as well. An example of medical apparatus is a fluoroscopic apparatus. Another example of medical apparatus is an X-ray CT apparatus. An example of apparatus for industrial use is a nondestructive inspecting apparatus.

In another aspect of the invention, a radiation detection signal processing method is provided for taking, at predetermined sampling time intervals, radiation detection signals generated by irradiating an object under examination, and performing a signal processing to obtain radiographic images based on the radiation detection signals outputted at the predetermined sampling time intervals, the method comprising the steps of:

removing lag-behind parts from the radiation detection signals by a recursive computation, on an assumption that a lag-behind part included in each of the radiation detection signals taken at the predetermined sampling time intervals is due to an impulse response formed of a single exponential function or a plurality of exponential functions with different attenuation time constants;

determining initial values for the recursive computation based on lag signal values remaining at a starting point of the recursive computation, when performing the recursive computation; and obtaining corrected radiation detection signals by removing the lag-behind parts through the recursive computation based on the initial values.

This radiation detection signal processing method allows the radiographic apparatus according to the invention to be implemented in an advantageous manner.

In the above radiation detection signal processing method, as in the radiographic apparatus that performs the recursive computation for removing the lag-behind part from each of the radiation detection signals, based on equations A-C, the recursive computation may be performed, with the initial values set, as follows, for example. The recursive computation for removing the lag-behind part from each of the radiation detection signals may be performed based on the following equations A-C:

$$X_k = Y_k - \sum_{n=1}^{N} [S_{nk}] \quad\quad A$$

$$T_n = -\Delta t/\tau_n \quad\quad B$$

$$S_{nk} = \exp(T_n) \cdot \{\alpha_n \cdot [1-\exp(T_n)] \cdot \exp(T_n) \cdot S_{n(k-1)}\} \quad\quad C$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n; the initial values are derived from the following equation D:

$$X_0 = 0, S_{n0} = \gamma_n \cdot Y_0 \quad\quad D$$

where $\gamma_n$: residual rate of component n of a certain attenuation time constant $\tau_n$; and $Y_0$: lag signal value remaining at an X-ray non-emission time which is the starting point of the recursive computation; and the corrected radiation detection signals are obtained by removing the lag-behind parts based on said impulse response derived from equations A-C, with conditions of the initial values determined from equation D.

Where the recursive computation for removing the lag-behind part from each of the radiation detection signals is based on equations A-C, the radiographic apparatus that performs the recursive computation based on equations A-C may be implemented in an advantageous manner.

A preferred example of setting each residual rate $\gamma_n$ is as follows. As in the preferred example of radiographic apparatus that sets each residual rate $\gamma_n$, each residual rate $\gamma_n$ may be set to satisfy conditions of the following equation E:

$$\sum_{n=1}^{N} [\gamma_n] \leq 1, 0 \leq \gamma_n \quad\quad E$$

where $\sum_{n=1}^{N} [\gamma_n]$: total of residual rates $\gamma_n$ of component n.

With the preferred example of setting each residual rate $\gamma_n$, the preferred example of radiographic apparatus that sets each residual rate $\gamma_n$ may be implemented in an advantageous manner.

A more specific, preferred example of setting each residual rate $\gamma_n$ is as follows. As in the specific preferred example of radiographic apparatus that sets each residual rate $\gamma_n$, equation E is set to satisfy conditions of $$\sum_{n=1}^{N} [\gamma_n] = 1 \quad\quad E'$$

and each residual rate $\gamma_n$ is set to satisfy conditions of $$\gamma_1 = \gamma_2 = \ldots = \gamma_n = \ldots = \gamma_{N-1} = \gamma_N \quad\quad F$$

whereby equation D is expressed by the following equation D':

$$S_{n0} = Y_0/N \quad\quad D'$$

Another specific, preferred example of setting each residual rate $\gamma_n$ is as follows. As in the other specific preferred example of radiographic apparatus that sets each residual rate $\gamma_n$, equation E is set to satisfy conditions of $$\sum_{n=1}^{N} [\gamma_n] < 1 \quad\quad E''$$

and residual rate $\gamma_M$ in component m of certain attenuation time constant $\tau_m$ and other residual rates $\gamma_N$ are set to satisfy the following expression G:

$$0 < \gamma_M < 1, \gamma_N = 0 \quad\quad G$$

Instead of using $\gamma_n$ noted above, $S_{n0}$ satisfying $0 < S_{n0} < Y_0$ may be determined as initial values. That is, the recursive computation for removing the lag-behind part from each of the radiation detection signals may be performed based on the following equations A-C:

$$X_k = Y_k - \sum_{n=1}^{N} [S_{nk}] \quad\quad A$$

$$T_n = -\Delta t/\tau_n \quad\quad B$$

$$S_{nk} = \exp(T_n) \cdot \{\alpha_n \cdot [1-\exp(T_n)] \cdot \exp(T_n) \cdot S_{n(k-1)}\} \quad\quad C$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

$S_{n0}$ satisfying $0 < S_{n0} < Y_0$ is determined as initial values; and the corrected radiation detection signals are obtained by removing the lag-behind parts based on said impulse response derived from equations A-C, with conditions of the initial values determined.

Equations a-c may be used in place of the above equations A-C. That is, the recursive computation for removing the lag-behind part from each of the radiation detection signals may be performed based on the following equations a-c:

$$X_k = Y_k - \sum_{n=1}^{N} \{\alpha_n \cdot [1-\exp(T_n)] \cdot \exp(T_n) \cdot S_{nk}\} \quad\quad a$$

$$T_n = -\Delta t/\tau_n \quad\quad b$$

$$S_{nk} = X_{k-1} + \exp(T_n) \cdot S_{n(k-1)} \quad\quad c$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

the initial values are derived from the following equation D:

$$X_0=0, S_{n0}=\gamma_n \cdot Y_0 \qquad D$$

where $\gamma_n$: residual rate of component n of a certain attenuation time constant $\tau_n$; and $Y_0$: lag signal value remaining at an X-ray non-emission time which is the starting point of the recursive computation; and the corrected radiation detection signals are obtained by removing the lag-behind parts based on said impulse response derived from equations a-c, with conditions of the initial values determined from equation D.

It is possible to combine the above example of determining $S_{n0}$ satisfying $0<S_{n0}<Y_0$ as initial values, and the example of using equation a-c. That is, the recursive computation for removing the lag-behind part from each of the radiation detection signals may be performed based on the following equations a-c:

$$X_k = Y_k - \sum_{n=1}^{N} \{\alpha_n \cdot [1-\exp(T_n)] \cdot \exp(T_n) \cdot S_{nk}\} \qquad a$$

$$T_n = -\Delta t/\tau_n \qquad b$$

$$S_{nk} = X_{k-1} + \exp(T_n) \cdot S_{n(k-1)} \qquad c$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

$S_{n0}$ satisfying $0<S_{n0}<Y_0$ is determined as initial values; and the corrected radiation detection signals are obtained by removing the lag-behind parts based on said impulse response derived from equations a-c, with conditions of the initial values determined.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A preferred embodiment of this invention will be described in detail hereinafter with reference to the drawings.

Figure 1:
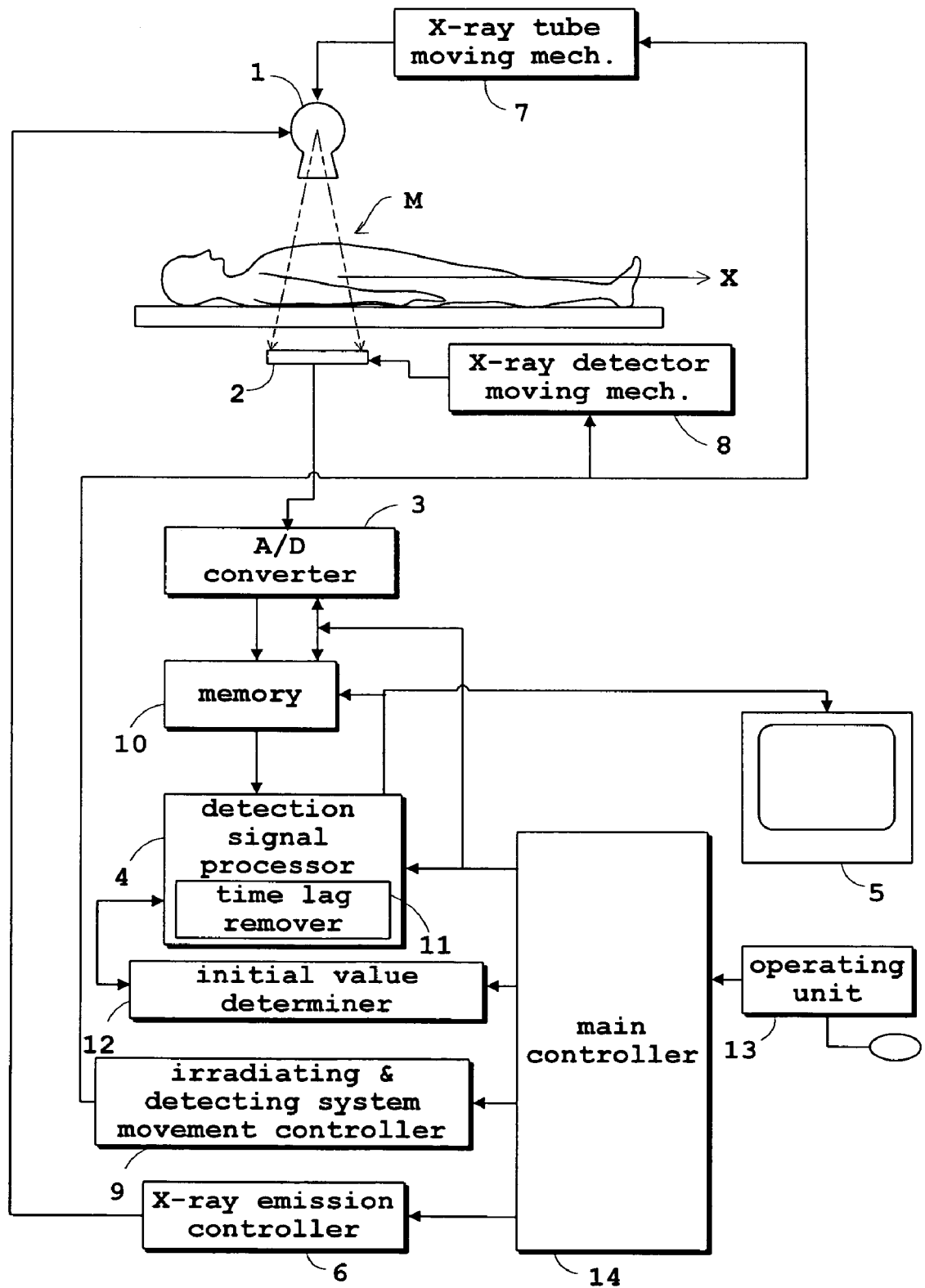
FIG. 1 is a block diagram showing an overall construction of a fluoroscopic apparatus according to the invention.

FIG. 1 is a block diagram showing an overall construction of a fluoroscopic apparatus according to this invention.

As shown in FIG. 1, the fluoroscopic apparatus includes an X-ray tube 1 for emitting X rays toward a patient M, an FPD (flat panel X-ray detector) 2 for detecting X rays transmitted through the patient M, an analog-to-digital converter 3 for digitizing X-ray detection signals taken from the FPD 2 at predetermined sampling time intervals $\Delta t$, a detection signal processor 4 for creating X-ray images based on X-ray detection signals outputted from the analog-to-digital converter 3, and an image monitor 5 for displaying the X-ray images created by the detection signal processor 4. That is, the apparatus is constructed to acquire X-ray images from the X-ray detection signals taken from the FPD 2 by the analog-to-digital converter 3 as the patient M is irradiated with X rays. The acquired X-ray images are displayed on the screen of the image monitor 5. Each component of this apparatus will particularly be described hereinafter. The X-ray tube 1 corresponds to the radiation emitting device in this invention. The FPD 2 corresponds to the radiation detecting device in this invention. The analog-to-digital converter 3 corresponds to the signal sampling device in this invention. The X-ray detection signals correspond to the radiation detection signals in this invention. The X-ray images correspond to the radiographic images in this invention.

The X-ray tube 1 and FPD 2 are opposed to each other across the patient M. Specifically, the X-ray tube 1 and FPD 2 are opposed to each other such that, in time of X-ray radiography, the X-ray tube 1 is controlled by an X-ray emission controller 6 to emit X rays in the form of a cone beam to the patient M and, at the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 7 and an X-ray detector moving mechanism 8, respectively. In moving the X-ray tube 1 and FPD 2, the X-ray tube moving mechanism 7 and X-ray detector moving mechanism 8 are controlled by an irradiating and detecting system movement controller 9 to move the X-ray tube 1 and FPD 2 together as opposed to each other, with the center of emission of X rays constantly in agreement with the center of the X-ray detecting surface of FPD 2. Of course, movement of the X-ray tube 1 and FPD 2 results in variations in the position of the patient M irradiated with X rays, hence movement of a radiographed site.

Figure 2:
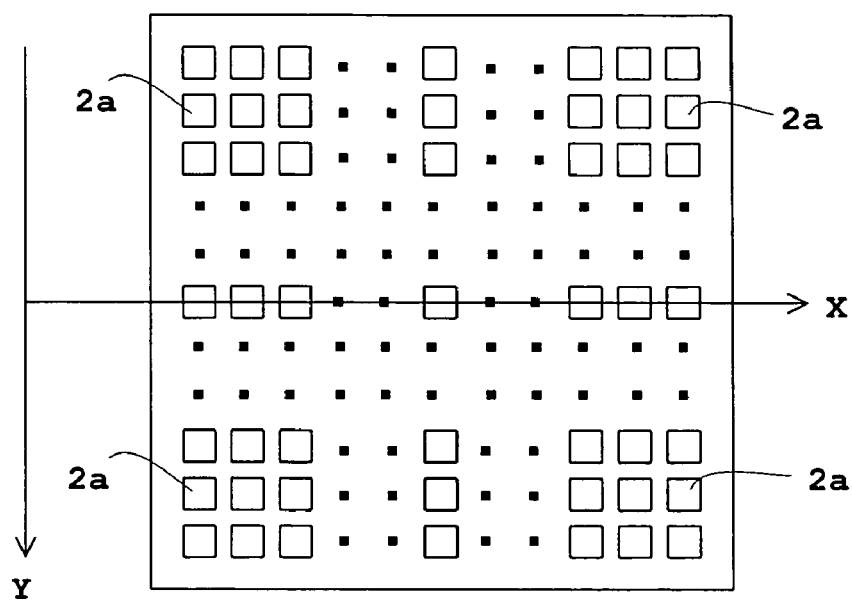
FIG. 2 is a plan view of an FPD used in the fluoroscopic apparatus.

As shown in FIG. 2, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1536 by 1536 on the X-ray detecting surface about 30 cm long and 30 cm wide. Each X-ray detecting element 2a of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface.

The analog-to-digital converter 3 continually takes X-ray detection signals for each X-ray image at sampling time intervals Δt, and stores the X-ray detection signals for X-ray image creation in a memory 10 disposed downstream of the converter 3. An operation for sampling (extracting) the X-ray detection signals is started before X-ray irradiation.

Figure 3:
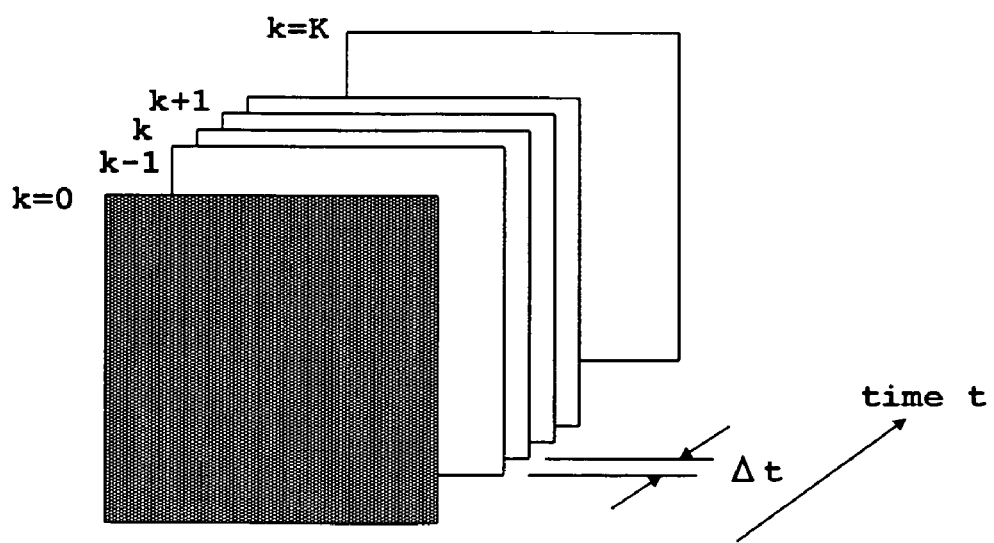
FIG. 3 is a schematic view showing a state of sampling X-ray detection signals during X-ray radiography by the fluoroscopic apparatus.

That is, as shown in FIG. 3, all X-ray detection signals for a penetration X-ray image are collected at each period between the sampling intervals Δt, and are successively stored in the memory 10. The sampling of X-ray detection signals by the analog-to-digital converter 3 before an emission of X rays may be started manually by the operator or automatically as interlocked with a command for X-ray emission.

As shown in FIG. 1, the fluoroscopic apparatus in this embodiment includes a time lag remover 11 for computing corrected radiation detection signals free from time lags, from the X-ray detection signals by a recursive computation, and an initial value determiner 12 for determining initial values for the recursive computation. The time lag remover 11 corresponds to the time lag removing device in this invention. The initial value determiner 12 corresponds to the initial value determining device in this invention.

A lag-behind part is included in each of the X-ray detection signals taken at the sampling time intervals from the FPD 2. The lag-behind part is removed from each X-ray detection signal by the above recursive computation based on an assumption that the lag-behind part is due to an impulse response formed of a single exponential function or a plurality of exponential functions with different attenuation time constants.

The initial value determiner 12 determines initial values for the recursive computation based on a lag signal value remaining at a starting point of the recursive computation. The starting point of the recursive computation refers to an X-ray non-emission time (k=0) for a first frame. The lag signal value remaining at the starting point of the recursive computation refers to lag signal value $Y_0$ remaining at the X-ray non-emission time. The time lag remover 11 removes lag-behind parts and obtains corrected radiation detection signals by the recursive computation based on the initial values determined by the initial value determiner 12.

Figure 7:
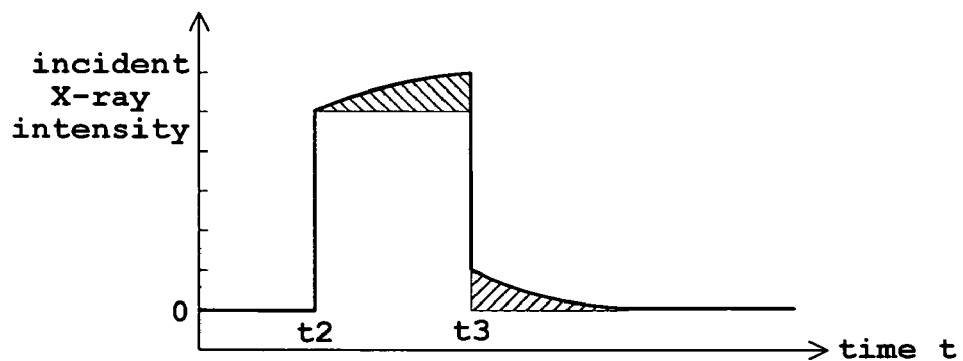
FIG. 7 is a view showing time lags corresponding to the radiation incidence of FIG. 6.

With the FPD 2, an X-ray detection signal generated at each point of time, as shown in FIG. 7, includes signals corresponding to preceding X-ray emissions and remaining as a lag-behind part (hatched part in FIG. 7). The time lag remover 11 removes this lag-behind part to produce a corrected, lag-free X-ray detection signal. Based on such lag-free X-ray detection signals, the detection signal processor 4 creates an X-ray image corresponding to a penetration X-ray image projected to the X-ray detecting surface.

Specifically, the time lag remover 11 performs a recursive computation for removing a lag-behind part from each X-ray detection signal by using the following equations A-C:

$$X_k = Y_k - \Sigma_{n=1}^{N}[S_{nk}] \quad\quad\quad A$$

$$T_n = -\Delta t/\tau_n \quad\quad\quad B$$

$$S_{nk} = \exp(T_n) \cdot \{\alpha_n \cdot [1-\exp(T_n)] \cdot \exp(T_n) \cdot S_{n(k-1)}\} \quad\quad\quad C$$

where Δt: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

The second term at the right side in equation A, that is equation C, "$S_{nk}=\exp(T_n) \cdot \{\alpha_n \cdot [1-\exp(T_n)] \cdot \exp(T_n) \cdot S_{n(k-1)}\}$" corresponds to the lag-behind part. Thus, the apparatus in this embodiment derives the corrected, lag-free X-ray detection signal $X_k$ promptly from equations A-C constituting a compact recurrence formula.

K is 0 at the starting point of the recursive computation, i.e. at X-ray non-emission time for the first frame. Values of $X_k$ and $S_{nk}$, i.e. initial values, in time of k=0 when performing the recursive computation are derived from the following equation D:

$$X_0 = 0, S_{n0} = \gamma_n \cdot Y_0 \quad\quad\quad D$$

where $\gamma_n$: residual rate of component n of a certain attenuation time constant $\tau_n$; and $Y_0$: lag signal value remaining at an X-ray non-emission time which is the starting point of the recursive computation.

Figure 8:
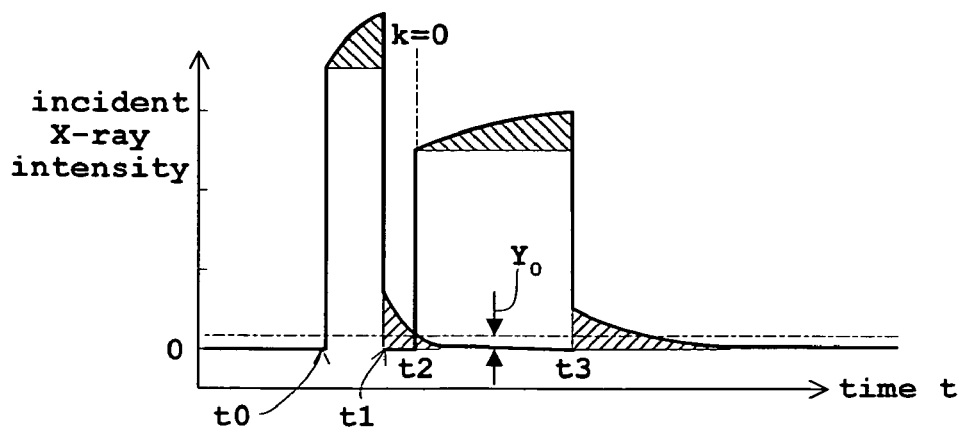
FIG. 8 is a view showing a time lag situation where a lag (i.e. a lag-behind part) in radiography overlaps fluoroscopy.

As shown in FIG. 8, for example, when a lag of photography during time t0-t1 overlaps fluoroscopy, a residual lag (lag signal value) due to a lag-behind part generated from the photography during time t0-t1 exists at an X-ray non-emission time which is the starting point of the recursive computation (k=0 in FIG. 8). That is, at the X-ray non-emission time, initial value $Y_0$ of X-ray detection signal $Y_k$ is not 0.

Thus, initial values for the recursive computation are set to $X_0=0$ and $S_{n0}=\gamma_n \cdot Y_0$ as in equation D ($Y_0$: lag signal value remaining at an X-ray non-emission time which is the starting point of the recursive computation). With the conditions of the initial values derived from equation D, the lag-behind part is removed based on the impulse response derived from equations A-C, to obtain corrected X-ray detection signal $X_k$.

In this embodiment, the analog-to-digital converter 3, detection signal processor 4, X-ray emission controller 6, irradiating and detecting system movement controller 9, time lag remover 11 and initial value determiner 12 are operable on instructions and data inputted from an operating unit 13 or on various commands outputted from a main controller 14 with progress of X-ray radiography.

Figure 4:
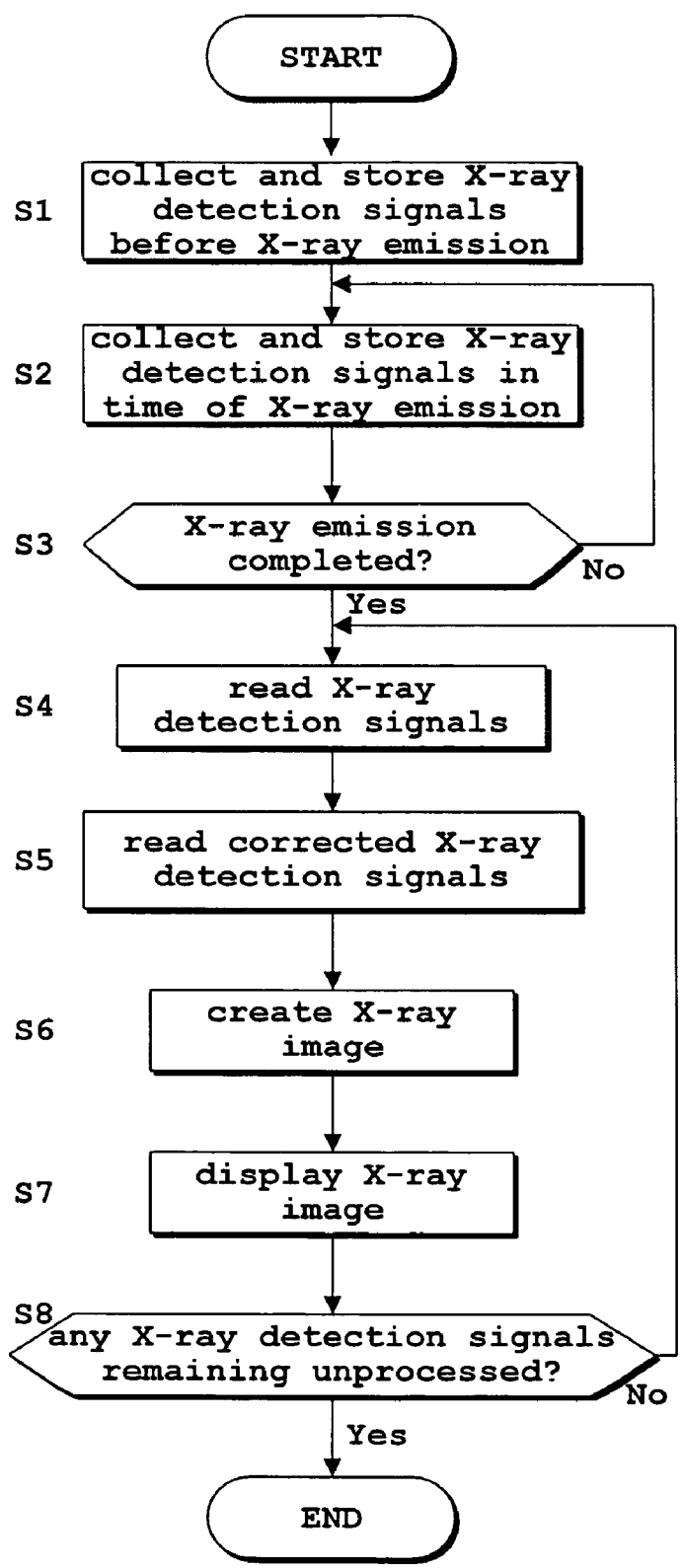
FIG. 4 is a flow chart showing a procedure of an X-ray detection signal processing method according to the invention.

Next, an operation for performing X-ray radiography with the apparatus in this embodiment will particularly be described with reference to the drawings. FIG. 4 is a flow chart showing a procedure of an X-ray detection signal processing method according to the invention. The illustrated radiography includes past radiography as shown in FIG. 8, as well as current fluoroscopy and radiography.

[Step S1] The analog-to-digital converter 3 starts taking X-ray detection signals $Y_k$ for one X-ray image from the FPD 2 at each period between the sampling time intervals $\Delta t$ ($=\frac{1}{30}$ second) before X-ray emission. The X-ray detection signals taken are stored in the memory 10.

[Step S2] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the memory 10.

[Step S3] When the X-ray emission is completed, the operation proceeds to step S4. When the X-ray emission is uncompleted, the operation returns to step S2.

[Step S4] X-ray detection signals $Y_k$ for one X-ray image collected in one sampling sequence are read from the memory 10.

[Step S5] The time lag remover 11 performs the recursive computation based on the equations A-C, and derives corrected X-ray detection signals $X_k$, i.e. pixel values, with lag-behind parts removed from the respective X-ray detection signals $Y_k$.

[Step S6] The detection signal processor 4 creates an X-ray image from the corrected X-ray detection signals $X_k$ for one sampling sequence (for one X-ray image).

[Step S7] The created X-ray image is displayed on the image monitor 5.

[Step S8] When unprocessed X-ray detection signals $Y_k$ remain in the memory 10, the operation returns to step S4. When no unprocessed X-ray detection signals $Y_k$ remain, the X-ray radiography is ended.

In this embodiment, the time lag remover 11 computes the corrected X-ray detection signals $X_k$ corresponding to the X-ray detection signals $Y_k$ for one X-ray image, and the detection signal processor 4 creates an X-ray image, both at sampling time intervals $\Delta t$ ($=\frac{1}{30}$ second). That is, the apparatus is constructed also for creating X-ray images one after another at a rate of about 30 images per second, and displaying the created X-ray images continuously. It is thus possible to perform a dynamic display of X-ray images.

Figure 5:
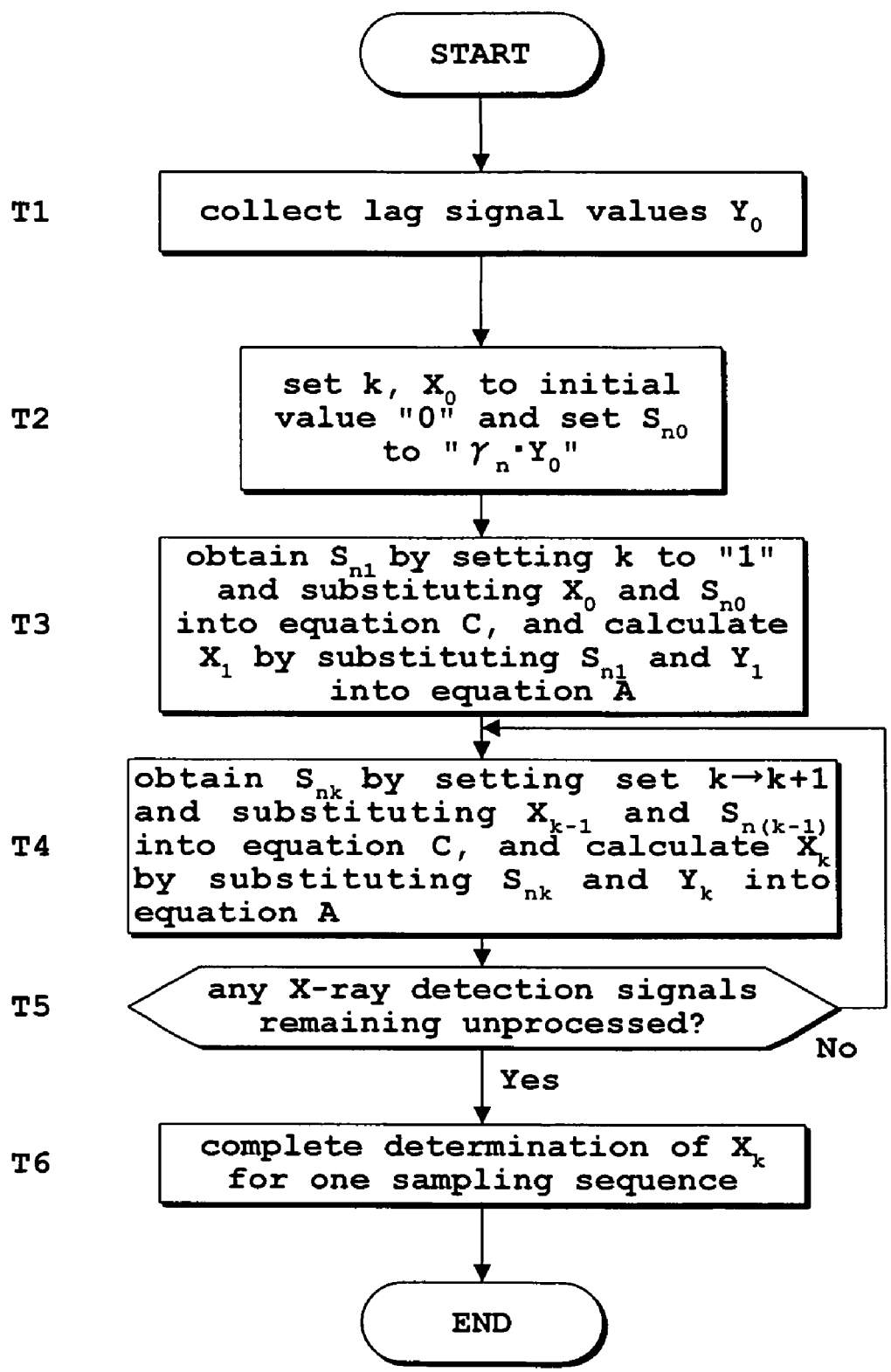
FIG. 5 is a flow chart showing a recursive computation process for time lag removal in the X-ray detection signal processing method.

Next, the process of recursive computation carried out in step S5 in FIG. 4 by the time lag remover 11 will be described with reference to FIG. 5. FIG. 5 is a flow chart showing a recursive computation process for time lag removal in the radiation detection signal processing method according to the invention.

[Step T1] The initial value determiner 12 collects residual lags (lag signal values) due to lag-behind parts generated in past photography. Specifically, for a first frame, the analog-to-digital converter 3 takes X-ray detection signals $Y_0$ for one X-ray image with residual lags from the FPD 2. These X-ray detection signals $Y_0$ are also lag signal values $Y_0$ remaining at an X-ray non-emission time which is the starting point of the recursive computation.

[Step T2] A setting k=0 is made, and $X_0$=0 in equation A is set as initial value. On the other hand, $S_{n0}$ for equation C is obtained by substituting lag signal value $Y_0$ acquired in step T1 into equation D. It is preferable to set residual rate $\gamma_n$ of component n of certain attenuation time constant $\tau_n$ to satisfy the conditions of the following equation E:

$$\Sigma_{n=1}^{N}[\gamma_n] \leq 1, 0 \leq \gamma_n \qquad E$$

where $\Sigma_{n=1}^{N}[\gamma_n]$: total of residual rates $\gamma_n$ of component n.

When the total of residual rates $\gamma_n$ of component n exceeds 1, the lag-behind parts can be removed excessively. Conversely, when the total of residual rates $\gamma_n$ of component n has a negative value, the lag-behind parts can be added. The lag-behind parts may be removed in an appropriate amount by setting the total of residual rate $\gamma_n$ of component n to 0 to 1 inclusive, and setting residual rate $\gamma_n$ to 0 or more. For equation E, the equation E' or equation E" set out below may be employed.

In the case of equation E', $$\Sigma_{n=1}^{N}[\gamma_n]=1 \qquad E'$$

equation E satisfies the conditions of equation E', and each residual rate $\gamma_n$ is set to satisfy the following equation F:

$$\gamma_1=\gamma_2=\ldots=\gamma_n=\ldots=\gamma_{N-1}=\gamma_N \qquad F$$

Equation F is substituted into equation E' to obtain $N \cdot \gamma_N=1$. Therefore, each residual rate $\gamma_n$ becomes $\gamma_N=1/N$, and residual rates $\gamma_n$ are evenly distributed by the number N of exponential functions (with different time constants constituting the impulse response). Thus, by substituting $\gamma_N=1/N$ for $S_{n0}=\gamma_n \cdot Y_0$ in equation D, equation D is expressed by the following equation D':

$$S_{n0}=Y_0/N \qquad D'$$

When the number of exponential functions is three (N=3), $S_{10}$, $S_{20}$ and $S_{30}$ are all set to $Y_0/3$ based on equation D.

In the case of equation E", $$\Sigma_{n=1}^{N}[\gamma_n]<1 \qquad E''$$

equation E satisfies the conditions of equation E", and residual rate $\gamma_M$ in component m of certain attenuation time constant $\tau_m$ and the other residual rates $\gamma_N$ are set to satisfy the following expression G:

$$0<\gamma_M<1, \gamma_N=0 \qquad G$$

When the number of exponential functions is three (N=3), residual rate $\gamma_2$ in component 2 of attenuation time constant $\tau_2$ satisfies $0<\gamma_2<1$ (e.g. $\gamma_2=0.1$), and the other residual rates satisfy $\gamma_1=\gamma_3=0$, $S_{10}$ and $S_{30}$ are set to 0 based on equation G, and $S_{20}$ is set to $\gamma_2 \cdot Y_0$ (e.g. $\gamma_2=0.1$) based on equation G.

[Step T3] In equations A and C, k=1 is set. That is, $S_{11}$, $S_{21}$ and $S_{31}$ are derived from equation C, i.e. $S_{n1}=\exp(T_1) \cdot \{\alpha_1 \cdot [1-\exp(T_1)] \cdot \exp(T_1) \cdot S_{n0}\}$. Further, a corrected X-ray detection signal $X_1$ is obtained by substituting $S_{11}$, $S_{21}$ and $S_{31}$ derived and X-ray detection signal $Y_1$ into equation A.

[Step T4] After incrementing k by 1 (k=k+1) in equations A and C, $X_{k-1}$ of a preceding time is substituted into equation C, thereby obtaining $S_{1k}$, $S_{2k}$ and $S_{3k}$. Further, corrected X-ray detection signal $X_k$ is obtained by substituting $S_{1k}$, $S_{2k}$ and $S_{3k}$ derived and X-ray detection signal $Y_k$ into equation A.

[Step T5] When there remain unprocessed X-ray detection signals $Y_k$, the operation returns to step T4. When no unprocessed X-ray detection signals $Y_k$ remain, the operation proceeds to the next step T6.

[Step T6] Corrected X-ray detection signals $X_k$ for one sampling sequence (for one X-ray image) are obtained to complete the recursive computation for the one sampling sequence.

According to the fluoroscopic apparatus in this embodiment, as described above, the time lag remover 11 removes lag-behind parts through the recursive computation process based on the initial values determined by the initial value determiner 12, thereby to obtain corrected X-ray detection signals. The lag-behind parts can be removed by taking into consideration lag signal values remaining at the starting point of the recursive computation. The lag signal values are dependent on the characteristic of the FPD (flat panel X-ray detector) 2. By removing the lag-behind parts, with the lag signal values taken into consideration, the lag-behind parts are removed from the X-ray detection signals with increased accuracy, without being influenced by the characteristic of the FPD 2. Even where the FPD 2 has a somewhat poor lag characteristic, the invention provides also an advantage of reducing the lag-behind parts to a quantity negligible for practical purposes, to enlarge a permissible range of the lag characteristic of FPD 2, and improve the yield of FPD 2.

Figure 6:
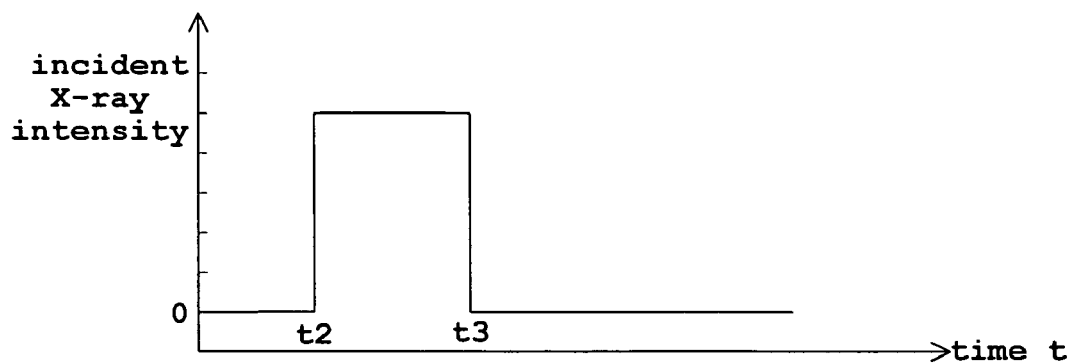
FIG. 6 is a view showing a state of radiation incidence.

This embodiment derives the corrected, lag-free X-ray detection signal $X_k$ promptly from equations A-C constituting a compact recurrence formula. When, as shown in FIG. 6, a fixed quantity of X rays enter the FPD 2 during time t2-t3, and provided that no time lag occurs with the FPD 2, the X-ray detection signal will have a fixed value as shown in FIG. 6.

In practice, however, the FPD 2 has a time lag to add a lag-behind part as shown in hatching in FIG. 7. Consequently, the X-ray detection signal $Y_k$ becomes as shown in thick lines in FIG. 7. In this embodiment, the second term at the right side in equation A, that is equation C "$S_{nk} = \exp(T_n) \cdot \{\alpha_n \cdot [1-\exp(T_n)] \cdot \exp(T_n) \cdot S_{n(k\_1)}\}$" corresponds to each lag-behind part shown in hatching in FIG. 7. Since the lag-behind part is deducted from X-ray detection signal $Y_k$, the corrected X-ray detection signal $X_k$ is free from the lag-behind part as shown in FIG. 6.

When, as shown in FIG. 8, a lag of photography performed during time t0-t1 overlaps fluoroscopy, a residual lag (lag signal value) due to a lag-behind part generated in the photography during time t0-t1 exists even at an X-ray non-emission time (k=0 in FIG. 8) which is a starting point of the recursive computation. That is, even though this is an X-ray non-emission time, the initial value $Y_0$ of X-ray detection signal $Y_k$ is not 0. Thus, initial values for the recursive computation are set to $X_0=0$ and $S_{n0}=\gamma_n \cdot Y_0$ as in equation D ($Y_0$: lag signal value remaining at the X-ray non-emission time which is a starting point of the recursive computation). With the conditions of the initial values derived from equation D, the lag-behind part is removed based on the impulse response derived from equations A-C, to obtain a corrected X-ray detection signal.

By removing the lag-behind parts, with the lag signal values taken into consideration as in equation D, the lag-behind parts are removed from X-ray detection signals with increased accuracy, without being influenced by the characteristic of the FPD 2.

This invention is not limited to the foregoing embodiment, but may be modified as follows:

(1) The embodiment described above employs an FPD as the radiation detecting device. This invention is applicable also to an apparatus having a radiation detecting device other than an FPD that causes time lags in X-ray detection signals.

(2) While the apparatus in the foregoing embodiment is a fluoroscopic apparatus, this invention is applicable also to an apparatus other than the fluoroscopic apparatus, such as an X-ray CT apparatus.

(3) The apparatus in the foregoing embodiment is designed for medical use. This invention is applicable not only to such medical apparatus but also to an apparatus for industrial use such as a nondestructive inspecting apparatus.

(4) The apparatus in the foregoing embodiment uses X rays as radiation. This invention is applicable also to an apparatus using radiation other than X rays (such as γ rays).

(5) In the foregoing embodiment, initial values are derived from equation D ($X_0=0$, $S_{n0}=\gamma_n \cdot Y_0$). Instead of using residual rate $\gamma_n$, $S_{n0}$ satisfying $0<S_{n0}<Y_0$ may be determined as initial values.

(6) In the foregoing embodiment, a lag-behind part is removed based on the impulse response derived from equations A-C, with the conditions of initial values derived from equation D, to obtain a corrected X-ray detection signal. As also described in relation to the technique disclosed in Japanese Unexamined Patent Publication No. 2004-242741, the conditions of initial values derived from equation D may be applied when removing a lag-behind part based on the impulse response derived from equations a-c. That is, a lag-behind part may be removed based on the impulse response derived from equations a-c, with the conditions of initial values derived from equation D, to obtain a corrected X-ray detection signal.

(7) In the foregoing embodiment, each residual rate $\gamma_n$, preferably, is set to satisfy the conditions of equation E ($\Sigma_{n=1}^{N} [\gamma_n] \leq 1$, $0 \leq \gamma_n$). In an example of satisfying the conditions of equation E, the conditions of equation E' ($\Sigma_{n=1}^{N} [\gamma_n]=1$) is satisfied and each residual rate $\gamma_n$ is set to satisfy the conditions of equation F ($\gamma_1=\gamma_2=\ldots=\gamma_n=\ldots=\gamma_{N-1}=\gamma_N$). In another example of satisfying the conditions of equation E, the conditions of equation E'' ($\Sigma_{n=1}^{N} [\gamma_n]<1$) is satisfied and residual rate $\gamma_M$ in component m of certain attenuation time constant $\tau_m$ and the other residual rates $\gamma_N$ are set to satisfy the conditions of expression G ($0<\gamma_M<1$, $\gamma_N=0$). The above particulars are not limitative as long as the conditions of equation E are satisfied.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining radiographic images based on radiation detection signals, comprising:

radiation emitting means for emitting radiation toward an object under examination;

radiation detecting means for detecting radiation transmitted through the object under examination; and signal sampling means for taking radiation detection signals from the radiation detecting means at predetermined sampling time intervals;

said apparatus obtaining radiographic images based on the radiation detection signals outputted from the radiation detecting means at the predetermined sampling time intervals as radiation is emitted to the object under examination;

said apparatus further comprising:

time lag removing means for removing lag-behind parts from the radiation detection signals by a recursive computation, on an assumption that a lag-behind part included in each of said radiation detection signals taken at the predetermined sampling time intervals is due to an impulse response formed of a single exponential function or a plurality of exponential functions with different attenuation time constants; and initial value determining means for determining initial values for the recursive computation based on lag signal values remaining at a starting point of the recursive computation;

wherein said time lag removing means is arranged to obtain corrected radiation detection signals by removing the lag-behind parts from the radiation detection signals through the recursive computation based on the initial values determined by the initial value determining means.

2. A radiographic apparatus as defined in claim 1, wherein said time lag removing means is arranged to perform the recursive computation for removing the lag-behind part from each of the radiation detection signals, based on the following equations A-C:

$$X_k = Y_k - \Sigma_{n=1}^N [S_{nk}] \quad \quad A$$

$$T_n = -\Delta t / \tau_n \quad \quad B$$

$$S_{nk} = \exp(T_n) \cdot \{\alpha_n \cdot [1 - \exp(T_n)] \cdot \exp(T_n) \cdot S_{n(k-1)}\} \quad \quad C$$

where $\Delta t$: the sampling time interval;
k: a subscript representing a k-th point of time in a sampling time series;
$Y_k$: an X-ray detection signal taken at the k-th sampling time;
$X_k$: a corrected X-ray detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: an intensity of exponential function n; and
$\tau_n$: an attenuation time constant of exponential function n; and the initial value determining means is arranged to derive the initial values from the following equation D:

$$X_0 = 0, S_{n0} = \gamma_n \cdot Y_0 \quad \quad D$$

where $\gamma_n$: residual rate of component n of a certain attenuation time constant $\tau_n$; and
$Y_0$: lag signal value remaining at an X-ray non-emission time which is the starting point of the recursive computation;
and obtain the corrected radiation detection signals by removing the lag-behind parts based on said impulse response derived from equations A-C, with conditions of the initial values determined from equation D.

3. A radiographic apparatus as defined in claim 2, wherein each residual rate $\gamma_n$ is set to satisfy conditions of the following equation E:

$$\Sigma_{n=1}^N [\gamma_n] \leq 1, 0 \leq \gamma_n \quad \quad E$$

where $\Sigma_{n=1}^N [\gamma_n]$: total of residual rates $\gamma_n$ of component n.

4. A radiographic apparatus as defined in claim 3, wherein equation E is set to satisfy conditions of $$\Sigma_{n=1}^N [\gamma_n] = 1 \quad \quad E'$$

and each residual rate $\gamma_n$ is set to satisfy conditions of $$\gamma_1 = \gamma_2 = \ldots = \gamma_n = \ldots = \gamma_{N-1} = \gamma_N \quad \quad F$$

whereby equation D is expressed by the following equation D':

$$S_{n0} = Y_0 / N \quad \quad D'$$

5. A radiographic apparatus as defined in claim 3, wherein equation E is set to satisfy conditions of $$\Sigma_{n=1}^N [\gamma_n] < 1 \quad \quad E''$$

and residual rate $\gamma_M$ in component m of certain attenuation time constant $\tau_m$ and other residual rates $\gamma_N$ are set to satisfy the following expression G:

$$0 < \gamma_M < 1, \gamma_N = 0 \quad \quad G$$

6. A radiographic apparatus as defined in claim 1, wherein said radiation detecting means is a flat panel X-ray detector having numerous X-ray detecting elements arranged longitudinally and transversely on an X-ray detecting surface.

7. A radiographic apparatus as defined in claim 1, wherein said apparatus is a medical apparatus.

8. A radiographic apparatus as defined in claim 7, wherein said medical apparatus is a fluoroscopic apparatus.

9. A radiographic apparatus as defined in claim 7, wherein said medical apparatus is an X-ray CT apparatus.

10. A radiographic apparatus as defined in claim 1, wherein said apparatus is for industrial use.

11. A radiographic apparatus as defined in claim 10, wherein said apparatus for industrial use is a nondestructive inspecting apparatus.

12. A radiation detection signal processing method for taking, at predetermined sampling time intervals, radiation detection signals generated by irradiating an object under examination, and performing a signal processing to obtain radiographic images based on the radiation detection signals outputted at the predetermined sampling time intervals, said method comprising the steps of:
removing lag-behind parts from the radiation detection signals by a recursive computation, on an assumption that a lag-behind part included in each of said radiation detection signals taken at the predetermined sampling time intervals is due to an impulse response formed of a single exponential function or a plurality of exponential functions with different attenuation time constants;
determining initial values for the recursive computation based on lag signal values remaining at a starting point of the recursive computation, when performing the recursive computation; and
obtaining corrected radiation detection signals by removing the lag-behind parts through the recursive computation based on the initial values.

13. A radiation detection signal processing method as defined in claim 12, wherein the recursive computation for removing the lag-behind part from each of the radiation detection signals is performed based on the following equations A-C:

$$X_k = Y_k - \Sigma_{n=1}^N [S_{nk}] \quad \quad A$$

$$T_n = -\Delta t / \tau_n \quad \quad B$$

$$S_{nk} = \exp(T_n) \cdot \{\alpha_n \cdot [1 - \exp(T_n)] \cdot \exp(T_n) \cdot S_{n(k-1)}\} \quad \quad C$$

where $\Delta t$: the sampling time interval;
k: a subscript representing a k-th point of time in a sampling time series;
$Y_k$: an X-ray detection signal taken at the k-th sampling time;
$X_k$: a corrected X-ray detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;

$\alpha_n$: an intensity of exponential function n; and $\tau_n$: an attenuation time constant of exponential function n;

the initial values are derived from the following equation D:

$$X_0=0, S_{n0}=\gamma_n \cdot Y_0 \qquad \text{D}$$

where $\gamma_n$: residual rate of component n of a certain attenuation time constant $\tau_n$; and $Y_0$: lag signal value remaining at an X-ray non-emission time which is the starting point of the recursive computation; and the corrected radiation detection signals are obtained by removing the lag-behind parts based on said impulse response derived from equations A-C, with conditions of the initial values determined from equation D.

14. A radiation detection signal processing method as defined in claim 13, wherein each residual rate $\gamma_n$ is set to satisfy conditions of the following equation E:

$$\Sigma_{n=1}^{N}[\gamma_n] \leq 1, 0 \leq \gamma_n \qquad \text{E}$$

where $\Sigma_{n=1}^{N}[\gamma_n]$: total of residual rates $\gamma_n$ of component n.

15. A radiation detection signal processing method as defined in claim 14, wherein equation E is set to satisfy conditions of $$\Sigma_{n=1}^{N}[\gamma_n]=1 \qquad \text{E'}$$

and each residual rate $\gamma_n$ is set to satisfy conditions of $$\gamma_1=\gamma_2=\ldots=\gamma_n=\ldots=\gamma_{N-1}=\gamma_N \qquad \text{F}$$

whereby equation D is expressed by the following equation D':

$$S_{n0}=Y_0/N \qquad \text{D'}$$

16. A radiation detection signal processing method as defined in claim 14, wherein equation E is set to satisfy conditions of $$\Sigma_{n=1}^{N}[\gamma_n]<1 \qquad \text{E''}$$

and residual rate $\gamma_M$ in component m of certain attenuation time constant $\tau_m$ and other residual rates $\gamma_N$ are set to satisfy the following expression G:

$$0<\gamma_M<1, \gamma_N=0 \qquad \text{G}$$

17. A radiation detection signal processing method as defined in claim 12, wherein the recursive computation for removing the lag-behind part from each of the radiation detection signals is performed based on the following equations A-C:

$$X_k=Y_k-\Sigma_{n=1}^{N}[S_{nk}] \qquad \text{A}$$

$$T_n=-\Delta t/\tau_n \qquad \text{B}$$

$$S_{nk}=\exp(T_n)\cdot\{\alpha_n\cdot[1-\exp(T_n)]\cdot\exp(T_n)\cdot S_{n(k-1)}\} \qquad \text{C}$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

$S_{n0}$ satisfying $0<S_{n0}<Y_0$ is determined as initial values; and the corrected radiation detection signals are obtained by removing the lag-behind parts based on said impulse response derived from equations A-C, with conditions of the initial values determined.

18. A radiation detection signal processing method as defined in claim 12, wherein the recursive computation for removing the lag-behind part from each of the radiation detection signals is performed based on the following equations a-c:

$$X_k=Y_k-\Sigma_{n=1}^{N}\{\alpha_n\cdot[1-\exp(T_n)]\cdot\exp(T_n)\cdot S_{nk}\} \qquad \text{a}$$

$$T_n=-\Delta t/\tau_n \qquad \text{b}$$

$$S_{nk}=X_{k-1}+\exp(T_n)\cdot S_{n(k-1)} \qquad \text{c}$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

the initial values are derived from the following equation D:

$$X_0=0, S_{n0}=\gamma_n \cdot Y_0 \qquad \text{D}$$

where $\gamma_n$: residual rate of component n of a certain attenuation time constant $\tau_n$; and $Y_0$: lag signal value remaining at an X-ray non-emission time which is the starting point of the recursive computation; and the corrected radiation detection signals are obtained by removing the lag-behind parts based on said impulse response derived from equations a-c, with conditions of the initial values determined from equation D.

19. A radiation detection signal processing method as defined in claim 12, wherein the recursive computation for removing the lag-behind part from each of the radiation detection signals is performed based on the following equations a-c:

$$X_k=Y_k-\Sigma_{n=1}^{N}\{\alpha_n\cdot[1-\exp(T_n)]\cdot\exp(T_n)\cdot S_{nk}\} \qquad \text{a}$$

$$T_n=-\Delta t/\tau_n \qquad \text{b}$$

$$S_{nk}=X_{k-1}+\exp(T_n)\cdot S_{n(k-1)} \qquad \text{c}$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

$S_{n0}$ satisfying $0<S_{n0}<Y_0$ is determined as initial values; and the corrected radiation detection signals are obtained by removing the lag-behind parts based on said impulse response derived from equations a-c, with conditions of the initial values determined.

* * * * *